United States Patent [19]

Matsumoto et al.

[11] 4,382,937
[45] May 10, 1983

[54] NAPHTHYRIDINE DERIVATIVES AND THEIR USE AS ANTI-BACTERIALS

[75] Inventors: Jun-ichi Matsumoto, Ikoma; Shinichi Nakamura, Takatsuki, both of Japan

[73] Assignees: Dainippon Pharmaceutical Co., Ltd., Osaka, Japan; Laboratoire Roger Bellon, Neuilly-sur-Seine, France

[21] Appl. No.: 351,924

[22] Filed: Feb. 24, 1982

[30] Foreign Application Priority Data

Feb. 27, 1981 [JP] Japan .................................. 56/28978
Mar. 6, 1981 [JP] Japan .................................. 56/32745

[51] Int. Cl.³ .................... A61K 31/44; C07D 471/04
[52] U.S. Cl. .................................... 424/256; 546/123
[58] Field of Search ........................ 546/123; 424/256

[56] References Cited

FOREIGN PATENT DOCUMENTS 27752 4/1981 European Pat. Off. .

*Primary Examiner*—John M. Ford
*Assistant Examiner*—Bernard Dentz

*Attorney, Agent, or Firm*—Wenderoth, Lind & Ponack

[57] ABSTRACT

A 1,8-naphthyridine compound of the formula

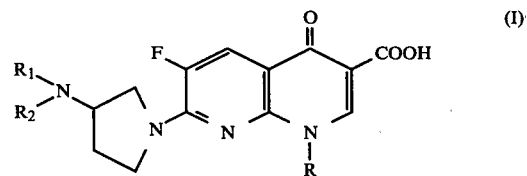

wherein
R is a vinyl or 2-fluoroethyl group, and
$R_1$ and $R_2$ are the same or different and each represents a hydrogen atom or a lower alkyl group having 1 to 4 carbon atoms, and the esters thereof and salts thereof. For example, 7-(3-amino-1-pyrrolidinyl)-6-fluoro-1,4-dihydro-4-oxo-1-vinyl-1,8-naphthyridine-3-carboxylic acid and non-toxic salts thereof, which are covered by the aforesaid compound, are useful as an antibacterial agent.

4 Claims, No Drawings

NAPHTHYRIDINE DERIVATIVES AND THEIR USE AS ANTI-BACTERIALS

This invention relates to novel naphthyridine derivatives having very high antibacterial activity, their intermediates, compositions containing these compounds as an active ingredient, and also to their use.

The present invention provides compounds of the following formula

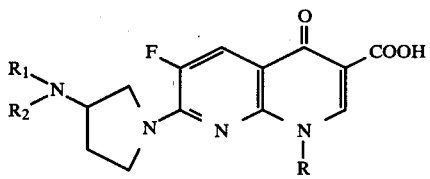

wherein
R is a vinyl or 2-fluoroethyl group, and
$R_1$ and $R_2$ are the same or different and each represents a hydrogen atom or a lower alkyl group having 1 to 4 carbon atoms,
and the esters thereof and the salts thereof.

The esters of the compounds [I] denote lower alkyl esters such as methyl ester and ethyl ester, or other esters which can be easily converted to the compound [I] by chemical hydrolysis or by enzymatic hydrolysis in a living body, such as pivaloyloxymethyl ester, ethoxycarbonyloxyethyl ester, 5-indanyl ester or phthalidyl ester.

The compounds [I] can exist as a hydrate, too. Accordingly, the present invention includes hydrates of the compounds represented by formula [I].

The salts of the compounds [I] denote salts formed between the compounds [I] and acids or bases. The acids may be various inorganic and organic acids. Examples of suitable acids are hydrochloric acid, acetic acid, lactic acid, succinic acid, lactobionic acid, gultamic acid, aspartic acid and methanesulfonic acid. The bases may be any inorganic or organic bases capable of forming salts with the carboxyl group of the compounds [I]. Examples of suitable bases are metal carbonates such as sodium or potassium carbonate.

It is an object of this invention to provide novel naphthyridine compounds having very high antibacterial activities, especially against Gram-negative bacteria including bacteria belonging to the genus Pseudomonas.

Another object of this invention is to provide a composition containing such a novel naphthyridine compound.

These and other objects of this invention become apparent from the following description.

Among the compounds of the present invention, preferred are those of formula [I] in which R is a vinyl group. Especially, compound 1 of the following formula and its salts are most preferred as an antibacterial agent.

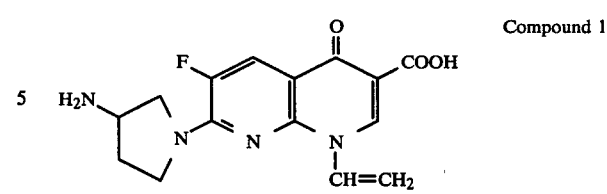

As structurally similar compound to the compound 1 of this invention, Japanese Laid-Open Patent Publication No. 31042/80 (published Mar. 5, 1980) discloses a naphthyridine derivative of following formula.

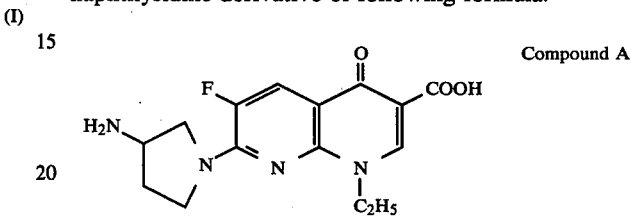

Investigations of the present inventors have shown that, as shown in Tables II to V given hereinbelow, compound 1 of the present invention have much better in vivo antibacterial efficacy against Gram-negative bacteria than the compound A.

The compounds of the present invention can be prepared by reacting a compound of formula [II]

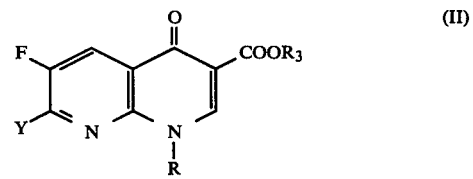

wherein
Y is a halogen atom or a lower alkylsulfonyl group,
$R_3$ is a hydrogen atom or a lower alkyl group having 1 to 6 carbon atoms, and
R is the same as defined above,
with a compound of formula

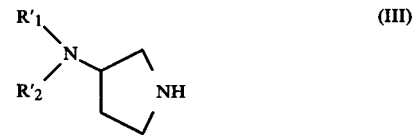

wherein
$R_1'$ and $R_2'$ are the same or different and each represents a hydrogen atom, a lower alkyl group having 1 to 4 carbon atoms or an amino-protecting group, and when the reaction product has an amino-protecting group corresponding to $R_1'$ and/or $R_2'$, converting said amino-protecting group to hydrogen by hydrolysis.

Examples of the amino-protecting group are acyl groups such as acetyl or trifluoroacetyl or lower alkoxycarbonyl groups such as ethoxycarbonyl.

The reaction of the compound [II] with the compound [III] is preferably carried out in an inert medium such as ethanol, acetonitrile, dioxane, dimethylformamide, toluene or xylene at 20° C. to 180° C., preferably 50° C. to 150° C., for 5 to 120 minutes, usually 20 to 60 minutes with stirring. It is sufficient that the amount of the pyrrolidine derivative [III] is stoichiometric to the compound [II]. Usually, however, a slight excess of the compound [III] (1.1 to 1.2 mols) is used. Furthermore, the compound [III] may be used in excess to make itself serve also as an acid-acceptor.

Depending upon the type of the substituents or the reaction conditions, the compound in which $R_1'$ and/or $R_2'$ is an amino-protecting group may undergo conversion to the compound in which $R_1'$ and/or $R_2'$ is hydrogen. When the reaction product obtained from the compound [II] and the compound [III] still has the amino-protecting group, the amino-protecting group can be converted to hydrogen by hydrolysis (deprotecting reaction).

The hydrolysis is carried out by contacting the reaction product having the amino-protecting group with water. It is generally carried out in the presence of an acid such as hydrochloric acid or a base such as sodium hydroxide to accelerate and complete the reaction.

When a compound given according to these reactions is in the form of an ester, it can be converted to the compound [I] of the present invention by hydrolysis in a customary manner. On the other hand, if necessary, an ester of the compound [I] may be obtained by esterification of the compound [I] in accordance with a conventional manner.

The compounds thus prepared are isolated and purified in a customary manner. Depending upon the conditions of isolation and/or purification, the compounds are obtained in the form of a salt, free carboxylic acid or free amine. They may be converted to provide the compounds of the present invention in the desired form.

The starting compounds [II] are prepared in accordance with the method described in Reference Examples given hereinafter.

The novel compounds of the invention, as will be shown in Experiments A to F given hereinbelow, have excellent antibacterial activity and low toxicity.

Accordingly, the compounds of the invention, especially compound [I] and nontoxic salts thereof, can be used as drugs for the treatment or prevention of bacterial infections of warm-blooded animals including man. Of course, esters of the compound [I] are valuable not only as intermediates for synthesis of the compounds [I] but also as antibacterial agents if these esters can be easily transferred to the compound [I] in a living body.

Doses of the compounds of this invention may vary with the age, body weight and conditions of the subject, the administration route, the number of administrations or the like, but is in the range of 0.3 to 80 mg per kilogram of body weight per day, preferably 1.3 to 50 mg per kilogram of body weight per day. The dose may be divided and administered in two to several times per day. The administration route is oral or parenteral, preferably oral or topical.

The compounds of the present invention can be administered as it is, but usually in the form of a pharmaceutical preparation with pharmaceutical acceptable carrier or adjuvants. Specific examples of the form of pharmaceutical preparations are tablets, capsules, granules, fine granules, powders, syrups, etc. These pharmaceutical preparations are prepared in accordance with a customary manner. The adjuvants and the carrier are those which are usually used in the field of pharmaceutical preparation with the compounds of the present invention, such as starch, mannitol, crystalline cellulose, sodium carboxymethyl cellulose, or the like. They may further contain other therapeutically valuable substances according to the purpose of medication.

The pharmaceutical preparation of this invention, for examples tablets and capsules, may contain about 10 to about 700 mg of the compound of this invention per tablet or capsule. These amounts are not critical, and may be varied according to whether the required amount of the compound of this invention is administered at a time or dividedly.

The compounds of this invention may also be used as fish medicines, agricultural chemicals or food preservatives.

The processes for producing the novel compounds of the invention and their pharmacological activities are illustrated below.

Reference Examples 1 and 2 show processes for the preparation of the starting compounds.

Examples 1 to 6 illustrate processes for the preparation of the compounds of this invention.

Experiments A to F show the pharmacological activities of the compound of the invention.

Examples 7 and 8 show the preparations of pharmaceuticals containing the compound of this invention.

REFERENCE EXAMPLE 1

Preparation of the starting compound

A mixture of 7-(4-ethoxycarbonyl-1-piperazinyl)-6-fluoro-1,4-dihydro-4-oxo-1-vinyl-1,8-naphthyridine-3-carboxylic acid (78 g) and aqueous 20% sodium hydroxide (1,100 ml) was refluxed with stirring for 24 hours. After cooling, the resulting crystals were collected by filtration and washed with aqueous 10% sodium hydroxide (50 ml). The crystals were added to water (600 ml) and the mixture was heated at 90° C. and the acetic acid (50 ml) was added. After treatment with charcoal, the solution was acidified with concentrated hydrochloric acid (100 ml), and cooled in an ice-bath. The resulting crystals were collected by filtration, washed with water, and recrystallized from ethanol-chloroform to give 42.5 g of 6-fluoro-1,4-dihydro-7-hydroxy-4-oxo-1-vinyl-1,8-naphthyridine-3-carboxylic acid, m.p. 256°–259° C.

A mixture of the 7-hydroxy compound (6.5 g) thus obtained and phosphoryl chloride (60 ml) was heated at 120° C. with stirring for 5 minutes. After the reaction was completed, the phosphoryl chloride was evaporated under reduced pressure, and the residue was suspended in a mixture of ethanol (5 ml) and chloroform (30 ml). The suspension was diluted with water and shaken. The chloroform layer was separated, washed with water, and dried over anhydrous magnesium sulfate. The chloroform extract was concentrated to dryness, and the residue was crystallized from ethyl acetate (10 ml). The resulting crystals were collected by filtration. The crystals were chromatographed on silicagel followed by recrystallization from ethyl acetate to give 5.7 g of ethyl 7-chloro-6-fluoro-1,4-dihydro-4-oxo-1-vinyl-1,8-naphthyridine-3-carboxylate, m.p. 150°–151° C.

EXAMPLE 1

Preparation of the compound 1 and its salt

A mixture of 3-trifluoroacetylaminopyrrolidine (5.46 g), ethanol (60 ml) and triethylamine (3 g) was added to ethyl 7-chloro-6-fluoro-1,4-dihydro-4-oxo-1-vinyl-1,8-naphthyridine-3-carboxylate (5.93 g) obtained according to Reference Example 1. The mixture was heated under reflux for one hour. After ice-cooling, the resulting crystals were collected by filtration and washed with ethanol. Recrystallization of the crude crystals from ethanol-chloroform gave 7.5 g of ethyl 6-fluoro-7-(3-trifluoroacetylamino-1-pyrrolidinyl)-1,4-dihydro-4-oxo-1-vinyl-1,8-naphthyridine-3-carboxylate, m.p. 280°–282° C. A solution of the compound (4.4 g) thus obtained in 1 N sodium hydroxide (80 ml) was stirred for 2 hours at 60° C. At the same temperature the mixture was adjusted to pH 7–8 by addition of acetic acid. After ice-cooling, the resulting crystals were collected by filtration, washed with water, and dissolved in hot 10% acetic acid, followed by treating with charcoal.

The solution was again adjusted to pH 7.5 by addition of aqueous 10% sodium hydroxide. The resulting crystals were collected by filtration, washed with water, and dried to give 2.8 g of 7-(3-amino-1-pyrrolidinyl)-6-fluoro-1,4-dihydro-4-oxo-1-vinyl-1,8-naphthyridine-3-carboxylic acid (compound 1), m.p. 253°–257° C. with decomposition.

The compound 1 (1.59 g) thus obtained was suspended in a mixture of 1 N hydrochloric acid (5.4 ml) and ethanol (10 ml). The suspension was warmed at 60° C. for 15 minutes with stirring. The 35 ml of ethanol was added. After cooling, the resulting precipitate was collected by filtration, washed with ethanol, and dried. There were obtained 1.6 g of the hydrochloride of the compound 1, m.p. 282°–290° C. with decomposition.

An equimolar mixture of the compound 1 and L-aspartic acid was treated in water in a similar manner to give L-aspartate (as a mono-hydrate) of the compound 1, m.p. 235°–240° C. with decomposition.

EXAMPLE 2

Preparation of ethyl ester of the compound 1

To a cooled solution of 3-aminopyrrolidine (3.6 g) and triethylamine (4.2 g) in 100 ml of chloroform was added a solution of ethyl 7-chloro-6-fluoro-1,4-dihydro-4-oxo-1-vinyl-1,8-naphthyridine-3-carboxylate (4.15 g) in 50 ml of chloroform over a period of 40 minutes with stirring. The reaction mixture was kept under ice-cooling for one hour and then stirred for 4 hours at room temperature. To this mixture was added a mixture of water (50 ml) and 2 N sodium hydroxide (20 ml). The chloroform layer was separated from the reaction mixture, washed with water, and dried over anhydrous sodium sulfate. The chloroform was distilled off and the residue was triturated with ethyl acetate (20 ml). The resulting solid was collected and recrystallized from ethyl acetate to give 3.9 g of ethyl 7-(3-amino-1-pyrrolidinyl)-6-fluoro-1,4-dihydro-4-oxo-1,8-naphthyridine-3-carboxylate (ethyl ester of the compound 1) m.p. 139°–141° C.

EXAMPLE 3

Preparation of
6-fluoro-1,4-dihydro-7-(3-methylamino-1-pyrrolidinyl)-4-oxo-1-vinyl-1,8-naphthyridine-3-carboxylic acid (compound 2)

Ethyl 6-fluoro-7-[3-(N-trifluoroacetyl-N-methyl-)amino-1-pyrrolidinyl]-1,4-dihydro-4-oxo-1-vinyl-1,8-naphthyridine-3-carboxylate, m.p. 160°–161° C., recrystallized from ethyl acetate-isopropyl ether, which was prepared by the method according to Example 1, was hydrolyzed in aqueous 10% sodium hydroxide to give the compound 2, m.p. 265°–267° C. with decomposition.

REFERENCE EXAMPLE 2

Preparation of the starting compound

6-Amino-2-chloro-3-nitropyridine was allowed to react with ethanethiol to give 6-amino-2-ethylthio-3-nitropyridine (m.p. 131.5°–132° C.). The product was then treated with acetic anhydride to give 6-acetylamino-2-ethylthio-3-nitro-pyridine (m.p. 167.5°–168° C.). The nitro group of this product was reduced in a usual manner to the amino group. The amino compound, without purification, was dissolved in 42% tetrafluoroboric acid, and then diazotized by addition of sodium nitrite to give 6-acetylamino-2-ethylthio-3-pyridine-diazonium fluoroborate decomposing at 132°–133° C. The diazonium salt was subjected to Schiemann reaction under reflux in petroleum benzine. The reaction product was isolated and purified in a usual manner to give 6-acetylamino-2-ethylthio-3-fluoro-pyridine (m.p. 110°–113.5° C.). Then the product was allowed to react with ethyl ethoxymethylenemalonate to give diethyl N-(2-ethylthio-3-fluoro-6-pyridinyl)aminomethylenemalonate (m.p. 77.5°–78.5° C.), which was subjected to cyclization reaction to give ethyl 7-ethylthio-6-fluoro-1,4-dihydro-4-oxo-1,8-naphthyridine-3-carboxylate (m.p. 280°–284° C.). The 1,8-naphthyridine derivative thus obtained was treated with 2-fluoroethyl p-toluenesulfonate to give ethyl 7-ethylthio-6-fluoro-1-(2-fluoroethyl)-1,4-dihydro-4-oxo-1,8-naphthyridine-3-carboxylate (m.p. 271°–273° C.), which was then oxidized with m-chloroperbenzoic acid to give ethyl 7-ethylsulfonyl-6-fluoro-1-(2-fluoroethyl)-1,4-dihydro-4-oxo-1,8-naphthyridine-3-carboxylate (m.p. 176°–178° C.).

EXAMPLE 4

Preparation of
7-(3-amino-1-pyrrolidinyl)-6-fluoro-1-(2-fluoroethyl)-1,4-dihydro-4-oxo-1,8-naphthyridine-3-carboxylic acid (compound 3)

A mixture of ethyl 7-ethylsulfonyl-6-fluoro-1-(2-fluoroethyl)-1,4-dihydro-4-oxo-1,8-naphthyridine-3-carboxylate (19.8 g) obtained according to the Reference Example 2, 3-acetylaminopyrrolidine (10.2 g), triethylamine (7.4 ml), and ethanol (400 ml) was heated under reflux for 2 hours. After cooling, the resulting crystals were collected by filtration, and recrystallized from chloroform-ethanol to give 16.8 g of ethyl 7-(3-acetylamino-1-pyrrolidinyl)-6-fluoro-1-(2-fluoroethyl)-1,4-dihydro-4-oxo-1,8-naphthyridine-3-carboxylate melting at 269°–270° C. A solution of the above ester (15.0 g) in 20% hydrochloric acid (100 ml) was heated under reflux for 4 hours. After cooling, ethanol (100 ml) was added to the mixture and the resulting crystals were collected by filtration. The crystals were dissolved in hot water (100 ml) and treated with charcoal. The filtrate was adjusted to pH 8.5–9.0 by addition of aqueous 27% ammonia, and the resulting crystals were collected by filtration, washed with water, and dried to give 9.3 g of the compound 3, m.p. 251°–255° C.

EXAMPLE 5

Preparation of 6-fluoro-1-(2-fluoroethyl)-1,4-dihydro-7-(3-methylamino-1-pyrrolidinyl)-4-oxo-1,8-naphthyridine-3-carboxylic acid (compound 4)

A mixture of ethyl 7-ethylsulfonyl-6-fluoro-1-(2-fluoroethyl)-1,4-dihydro-4-oxo-1,8-naphthyridine-3-carboxylate (26.7 g) obtained according to the Reference Example 2, 3-(N-acetyl-N-methylamino)pyrrolidine (15.5 g), triethylamine (10.0 ml), and ethanol (300 ml) was heated under reflux for one hour. The reaction mixture was concentrated to a half volume under reduced pressure. To the mixture was added water (200 ml), and the resulting crystals were collected by filtration, and recrystallized from chloroform-ethanol to give 24.8 g of ethyl 7-[3-(N-acetyl-N-methylamino)-1-pyrrolidinyl]-6-fluoro-1-(2-fluoroethyl)-1,4-dihydro-4-oxo-1,8-naphthyridine-3-carboxylate melting at 227°–229° C. A solution of the above ester (20.0 g) in 20% hydrochloric acid (120 ml) was heated under reflux for 3 hours. After the reaction was completed, water (60 ml) and ethanol (120 ml) were added to the reaction mixture, and the resulting crystals were collected by filtration. The crystals were dissolved in hot water (800 ml) and the solution was treated with charcoal. The filtrate was adjusted to pH 8.5–9.0 by addition of 27% aqueous ammonia. The crystals were collected by filtration, washed with water, and dried to give 11.0 g of the compound 4, m.p. 243°–245° C.

EXAMPLE 6

Preparation of 7-(3-dimethylamino-1-pyrrolidinyl)-6-fluoro-1-(2-fluoroethyl)-1,4-dihydro-4-oxo-1,8-naphthyridine-3-carboxylic acid (compound 5)

The same reaction as in Example 4 was carried out using ethyl 7-ethylsulfonyl-6-fluoro-1-(2-fluoroethyl)-1,4-dihydro-4-oxo-1,8-naphthyridine-3-carboxylate and 3-dimethylaminopyrrolidine as starting materials. There was obtained the compound 5, m.p. 247°–249° C.

EXPERIMENT A

The minimum inhibitory concentrations (MIC: μg/ml) of the following compounds were measured by the twofold agar-dilution method according to the procedure described in Chemotherapy, Vol. 29, No. 1, page 76 (1981).

The results are shown in Table I.

COMPOUND 1

7-(3-Amino-1-pyrrolidinyl)-6-fluoro-1,4-dihydro-4-oxo-1-vinyl-1,8-naphthyridine-3-carboxylic acid

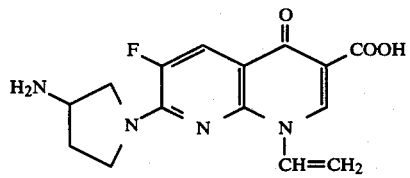

(the compound obtained by the procedure described in Example 1).

COMPOUND A 7-(3-Amino-1-pyrrolidinyl)-1-ethyl-6-fluoro-1,4-dihydro-4-oxo-1,8-naphthyridine-3-carboxylic acid

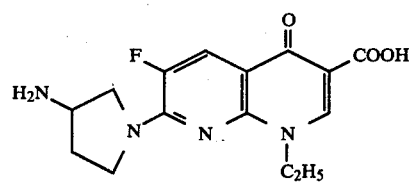

(the compound disclosed in Japanese Laid-Open Patent Publication No. 31042/80).

TABLE I

In vitro antibacterial activity against 12 strains of Gram-negative bacteria

| Bacteria | Compound 1 | Compound A |
|---|---|---|
| Escherichia coli NIHJ JC-2 | 0.025 | 0.1 |
| Escherichia coli P-5101 | 0.025 | 0.05 |
| Salmonella typhimurium S-9 | 0.05 | 0.1 |
| Salmonella enteritidis No. 1891 | 0.025 | 0.05 |
| Shigella flexneri 2a | 0.025 | 0.1 |
| Klebsiella pneumoniae No. 13 | 0.1 | 0.2 |
| Enterobacter cloacae 963 | 0.05 | 0.2 |
| Pseudomonas aeruginosa Tsuchiijima | 0.2 | 0.39 |
| Pseudomonas aeruginosa No. 12 | 0.2 | 0.39 |
| Serratia marcescens IFO 3736 | 0.2 | 0.2 |
| Proteus morganii Kono | 0.05 | 0.2 |
| Proteus mirabilis IFO 3849-4 | 0.2 | 0.39 |

EXPERIMENT B

In vivo therapeutic efficacy against systemic infections in mice

Compounds 1 and A were each suspended in a 0.2% aqueous solution of sodium carboxymethyl cellulose. Each of the solutions was orally administered to mice infected with each of the test organisms under the conditions described below, and the median effective doses ($ED_{50}$) obtained are shown in Table II.

EXPERIMENTAL CONDITIONS

Mice:
   Male mice (ddY) weighing about 20 g
Infection:
   (1) *Escherichia coli* P-5101:
      Intraperitoneal infection with about $9 \times 10^6$ cells per mouse suspended in trypto-soy broth with 4% mucin.
   (2) *Pseudomonas aeruginosa* No. 12:
      Intraperitoneal infection with about $4 \times 10^3$ cells per mouse suspended in trypto-soy broth with 4% mucin.
Medication:
   Twice, about 5 minutes and 6 hours after infection.
Observation:
   for 7 days.

TABLE II

In vivo efficacy against systemic infections in mice

| | Bacterium | |
|---|---|---|
| | *Escherichia coli* P-5101 | *Pseudomonas aeruginosa* No. 12 |
| | Route | |
| Compound | po | po |
| 1 | 0.8 | 1.8 |
| A | 1.6 | 6.7 |

Note:
The numerals in the table show $ED_{50}$ (mg/kg). $ED_{50}$ values were calculated in accordance with the Behrens-Kaerber method (Arch. Exp. Path. Pharm., 162, 480 (1931)).
po: oral administration.

EXPERIMENT C

In vivo therapeutic efficacy against pulmonary infection in mice

Female mice (ddY-S) weighing 18 to 26 g were intranasally intected with 4 drops of a bacterial suspension* in physiological saline. Drugs suspended in 0.2% sodium carboxymethyl cellulose were orally administered 0, 1, and 3 hours after infection. Survival rates were determined on the 5th day after infection. $ED_{50}$ was calculated by probit analysis.

*Pseudomonas aeruginosa No. 12—$2.0 \times 10^7$ cells/mouse

The results are shown in Table III.

TABLE III

In vivo efficacy against pulmonary infection with *Pseudomonas aeruginosa* No. 12 in mice

| Compound | Route | $ED_{50}$ (mg/kg) |
|---|---|---|
| 1 | po | 6.3 |
| A | po | 19.7 |

EXPERIMENT D

In vivo therapeutic efficacy against ascending kidney infection with *Pseudomonas aeruginosa* No. 12

Compounds 1 and A were tested by the following procedure for therapeutic efficacy against the ascending kidney infection with *Pseudomonas aeruginosa* No. 12 in mice.

Female mice (Std:ddY-S) weighing 22 to 30 g were anesthetized by intravenous injection of sodium pentobarbital at a dose of 50 mg/kg. Through a small suprapubic incision, the urinary bladder was exposed and then infected by injecting 0.1 ml of a 1:10,000 dilution of *Pseudomonas aeruginosa* No. 12 cultured for 20 hours in trypto-soy broth, using a 0.25 ml syringe with a 0.25 mm needle. The mice were restrained from drinking water for a period from 1 day before to 1 day after the infection. The compound 1 or A was administered orally twice a day for 3 days starting on the day of infection. On the 5th day after infection, the kidneys were harvested for the detection of the bacteria, transversely bisected and stamped on King A agar, which were incubated at 37° C. overnight. No bacterial finding in the kidneys was regarded as protected from the ascending kidney infection. $ED_{50}$ values were calculated by probit analysis.

The results are shown in Table IV.

TABLE IV

In vivo therapeutic efficacy against ascending kidney infection with *Pseudomonas aeruginosa* No. 12

| Compound | Route | $ED_{50}$ (mg/kg) |
|---|---|---|
| 1 | po | 0.5 |
| A | po | 3.0 |

EXPERIMENT E

In vivo therapeutic efficacy against dermal infections with *Pseudomonas aeruginosa* No. 12

Female mice (ddY-S) weighing 21 to 26 g were subcutaneously infected at the dorsal skin with approximate $9 \times 10^6$ viable cells of *Pseudomonas aeruginosa* No. 12 in 0.2 ml physiological saline. Medication was performed 6 times; 0, 3, 6, 24, 27, and 30 hours after infection. The appearance of skin abscess at the inoculated site was examined on the 4th day after infection and mice bearing no abscess were regarded as protected from the infection. $ED_{50}$ was calculated by probit analysis.

The results are shown in Table V.

TABLE V

In vivo therapeutic efficacy against dermal infection with *Pseudomonas aeruginosa* No. 12 in mice

| Compound | Route | $ED_{50}$ (mg/kg) |
|---|---|---|
| 1 | po | 2.4 |
| A | po | 11.7 |

EXPERIMENT F

Acute oral toxicity in mice

A solution containing compound 1 in various concentrations was orally given to male mice (ddY-S) at a volume of 0.1 ml per 10 g of body weight. The number of dead mice was counted after 7 days, and the value of median lethal dose ($LD_{50}$; mg/kg) was calculated in accordance with the Behrens-Kaerber method.

The $LD_{50}$ value of the compound 1 was more than 4,000.

EXAMPLE 7

| Compound 1 | 250 g |
|---|---|
| Starch | 50 g |
| Lactose | 35 g |
| Talc | 15 g |

The above components were blended and granulated and filled into 1,000 capsules in accordance with conventional methods.

EXAMPLE 8

| Compound 1 | 250 g |
|---|---|
| Starch | 54 g |
| Calcium carboxymethyl cellulose | 40 g |
| Microcrystalline cellulose | 50 g |
| Magnesium stearate | 6 g |

The above components were blended, granulated and made into tablets in a manner known per se. Thus, 1,000 tablets each weighing 400 mg were formed.

What we claim is:

1. A 1,8-naphthyridine compound of the formula

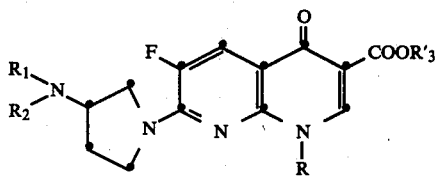

wherein

R is vinyl or 2-fluoroethyl, $R_1$ and $R_2$ are the same or different and each represents a hydrogen atom or lower alkyl having 1 to 4 carbon atoms, and $R_3'$ is a hydrogen atom, lower alkyl having 1 to 6 carbon atoms, pivaloyloxymethyl, ethoxycarbonyloxyethyl, 5-indanyl or phthalidyl or a non-toxic salt thereof.

2. 7-(3-amino-1-pyrrolidinyl)-6-fluoro-1,4-dihydro-4-oxo-1-vinyl-1,8-naphthyridine-3-carboxylic acid or a non-toxic salt thereof.

3. An antibacterial composition which comprises as an active ingredient an antibacterially effective amount of a 1,8-naphthyridine compound or non-toxic salt thereof as defined in claim 2 and a pharmaceutically acceptable carrier.

4. A method for the treatment of a bacterial infectious disease which comprises administering to a warm-blooded animal suffering from such disease an antibacterially effective amount of a 1,8-naphthyridine compound of the formula

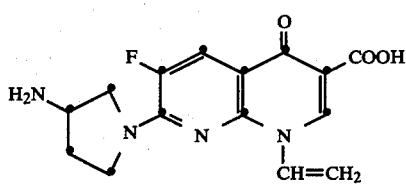

or a non-toxic salt thereof.